United States Patent
Kangas et al.

(10) Patent No.: US 8,168,213 B2
(45) Date of Patent: May 1, 2012

(54) MEDICAL DEVICES HAVING COATING WITH IMPROVED ADHESION

(75) Inventors: Steven Kangas, Woodbury, MN (US); Jan Seppala, Greenfield, MN (US); Peter G. Edelman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1290 days.

(21) Appl. No.: 11/803,433

(22) Filed: May 15, 2007

(65) Prior Publication Data
US 2008/0286333 A1 Nov. 20, 2008

(51) Int. Cl.
*A61F 2/02* (2006.01)
(52) U.S. Cl. .................................................. 424/423
(58) Field of Classification Search ............................ None
See application file for complete search history.

(56) References Cited

U.S. PATENT DOCUMENTS

| | | | |
|---|---|---|---|
| 6,545,097 B2 | 4/2003 | Pinchuk et al. | ............... 525/240 |
| 2003/0236514 A1 | 12/2003 | Schwarz | |
| 2005/0025802 A1 | 2/2005 | Richard et al. | ................. 424/423 |
| 2005/0085592 A1 | 4/2005 | Taniguchi et al. | ............. 525/242 |
| 2005/0272865 A1 | 12/2005 | Taniguchi et al. | ............. 525/71 |
| 2006/0093771 A1 | 5/2006 | Rypacek et al. | |
| 2008/0286326 A1 | 11/2008 | Benco | |

FOREIGN PATENT DOCUMENTS
EP 1493457 A1 1/2005

OTHER PUBLICATIONS

Pham et al, "Effects of Blending SIBS and SMA on Morphology and mechanical Properties", Materials Research Society Symposium Proceedings (2002), 734 (polymer/Metal Interfaces and Defect Mediated Phenomena in Ordered Polymers), 391-395, CODEAN: MRSPDM; ISSN; 0272-9172.*

T. Kowalewski et al., "Complex nanostructured materials from segmented copolymers prepared by ATRP," *Euro. Phys. J.E.*, vol. 10, (2003) pp. 5-16.

T. Caykara et al., "Composition of γ-ray induced triethoxyvinylsilane-methyl methacrylate copolymers determined by XPS", *Polymer*, vol. 39, No. 21 (1998) pp. 5269-5271.

R.E. Richard et al., "Evaluation of Acrylate-Based Block Coploymers Prepared by Atom Transfer Radical Polymerization as Matrices for Paclitaxel Delivery from Coronary Stents", *Biomacromolecules*, vol. 6 (2005) pp. 3410-3418. E. Bellman et al., "Hole Transport Polymers with Improved Interfacial Contact to the Anode Material", *Chem. Mater.*, vol. 12 (2000) pp. 1349-1353.

B. Reeves et al., "Recent Advances in Living Free Radical Polymerization", *University of Florida* Nov. 20, 2001, pp. 1-14.

Pyun and Matyjaszewski, "Synthesis of Nanocomposite Organic/Inorganic Hybrid Materials Using Controlled/"Living" Radical Polymerization", *Chem. Mater.*, vol. 13 (2001), pp. 3436-3448.

\* cited by examiner

*Primary Examiner* — Carlos Azpuru
(74) *Attorney, Agent, or Firm* — Mayer & Williams PC; David B. Bonham; Keum J. Park

(57) ABSTRACT

According to an aspect of the present invention, a medical device is provided which comprises a metallic substrate and polymeric region disposed over and in contact with the metallic substrate. The polymeric region comprises (a) a block copolymer that comprises (i) a hard polymer block that comprises a high Tg monomer and (ii) a soft polymer block that comprises a low Tg monomer, (b) an adhesion promoting copolymer that comprises (i) a first monomer that covalently or non-covalently bonds with the metallic substrate and (ii) a second monomer that is compatible with the low Tg monomer and/or the high Tg monomer and (c) a therapeutic agent. The polymeric region may further comprise an optional polymer that is used to tailor the release rate of the therapeutic agent.

41 Claims, 2 Drawing Sheets

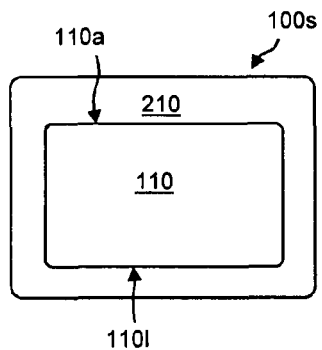 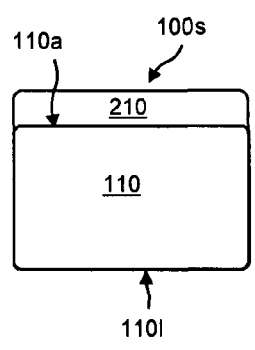 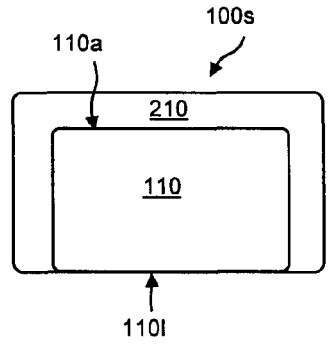
Fig. 2A    Fig. 2B    Fig. 2C
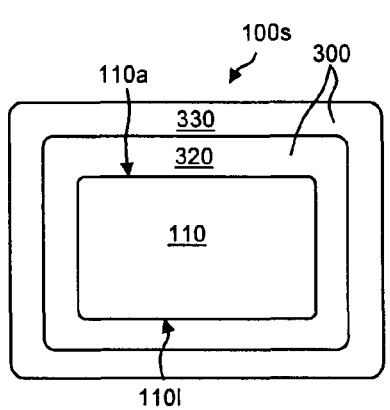 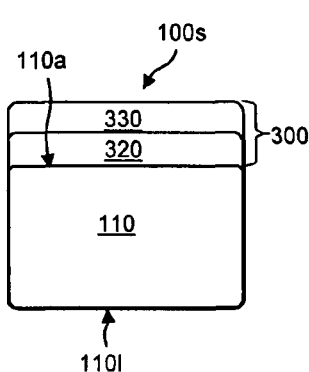 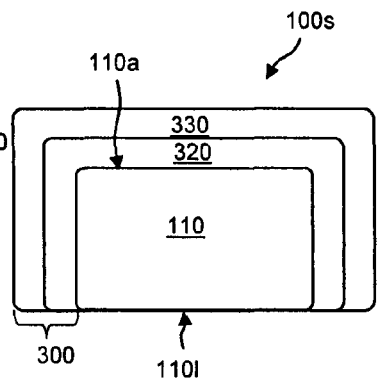
Fig. 3A    Fig. 3B    Fig. 3C

MEDICAL DEVICES HAVING COATING WITH IMPROVED ADHESION

FIELD OF THE INVENTION

The present invention relates generally to medical devices, and more particularly to implantable or insertable medical devices.

BACKGROUND OF THE INVENTION

Numerous polymer-based medical devices have been developed for implantation or insertion into the body. For example, various state of the art medical devices consist of a medical device substrate with a polymeric coating that serves as a reservoir for one or more therapeutic agents. Specific examples include drug eluting coronary stents, commercially available from Boston Scientific Corp. (TAXUS), Johnson & Johnson (CYPHER) and others, which have become the standard of care for maintaining vessel patency after balloon angioplasty. These products are based on metallic balloon expandable stents with polymeric coatings that release antiproliferative drugs at a controlled rate and total dose effective to inhibit the smooth muscle proliferation that is associated with restenosis (vessel reclosure).

Various types of polymeric materials have been used as drug-releasing reservoirs, including, for example, homopolymers such as poly(n-butyl methacrylate) and copolymers such as poly(ethylene-co-vinyl acetate), copolymers containing phosphoryl choline acrylate, and copolymers such as poly(isobutylene-co-styrene), for example, poly(styrene-b-isobutylene-b-styrene) triblock copolymers (SIBS), which are described, for instance, in U.S. Pat. No. 6,545,097 to Pinchuk et al. In addition to their utility as drug delivery reservoirs, SIBS copolymers have proven valuable for a variety of reasons, including their excellent biocompatibility, elasticity, strength, and processability. The latter characteristics are due, at least in part, to the fact that SIBS copolymers are thermoplastic elastomers. Thermoplastic elastomers are elastomeric (i.e., reversibly deformable) polymers that form physical crosslinks which can be reversed, for example, by dissolving or melting the polymer. SIBS triblock copolymers have an elastomeric low glass transition temperature (Tg) midblock and hard elevated Tg endblocks. As with many block copolymers, SIBS tends to phase separate, with the elastomeric blocks aggregating to form elastomeric phase domains and the hard blocks aggregating to form hard phase domains. It has been hypothesized that, because each elastomeric block has a hard block at each end, and because different hard blocks within the same triblock copolymer are capable of occupying two different or separate hard phase domains, the hard phase domains become physically crosslinked to one another via the soft blocks. Another embodiment of a phase separated thermoplastic elastomer consists of endblocks of polymethylmethacrylate and a midblock of polybutylacrylate (MBAM). The resulting desirable properties result from similar phase separation of the methacrylate hard blocks into hard block domains and the butylacrylate soft blocks into a soft block domain.

In a current process for forming TAXUS products, the outer surface of a stainless steel coronary stent is sprayed with a solution that contains solvent, paclitaxel and SIBS. The solution is sprayed on the outside of the stent, and to some degree, through the stent struts. The stent is ultimately encapsulated with the polymeric coating due to a combination of outside spraying and through-strut spraying combined with flow of the solution around the stent struts. The net result is that the spray process results in a conformal coating. The result of such a process is schematically illustrated, for example, in FIGS. 1A and 1B. FIG. 1A shows a stent 100 which contains a number of interconnected struts 100s. FIG. 1B is a cross-section taken along line b-b of strut 100s of stent 100 of FIG. 1A, and shows a stainless steel stent substrate 110 and a paclitaxel-containing polymeric coating 120, which encapsulates the substrate 110. The coating has relatively poor adhesion to the stent substrate surface. However, it is nonetheless well-secured to the stent substrate as a result of the encapsulation that occurs (and the inherent cohesive strength of SIBS).

While it is desirable to provide the abluminal surface of the stent with a polymeric coating that that is capable of releasing an antiproliferative drug to combat restenosis, such a drug may not be equally desirable on the luminal surface of the stent and, in fact, may even be detrimental to the extent that it may retard or otherwise interfere with the growth of healthy endothelial cells on the luminal surface of the stent. Moreover, the presence of a polymeric layer on the luminal surface is not needed for purposes of promoting biocompatibility, as various stent substrate materials, including stainless steel, are known to support endothelial cell growth. In addition, it may be desirable to minimize the total polymer content in a drug coated stent in order to minimize any potential undesirable biological responses to the polymer.

SUMMARY OF THE INVENTION

According to an aspect of the present invention, a medical device is provided which comprises a metallic substrate and polymeric region disposed over and in contact with the metallic substrate. The polymeric region comprises (a) a block copolymer that comprises (i) a hard polymer block that comprises a high Tg monomer and (ii) a soft polymer block that comprises a low Tg monomer, (b) an adhesion promoting copolymer that comprises (i) a first monomer that covalently or non-covalently bonds with the metallic substrate and (ii) a second monomer that is compatible with the low Tg monomer and/or the high Tg monomer and (c) a therapeutic agent.

For example, in some embodiments, the polymeric region comprises an adhesion promoting, polymeric drug release layer disposed over and in contact with the metallic substrate, which adhesion promoting polymeric drug release layer comprises the block copolymer, the adhesion promoting copolymer and the therapeutic agent.

As another example, in some embodiments, the polymeric region comprises (a) an adhesion promoting layer comprising the adhesion promoting copolymer disposed over and in contact with the substrate, and (b) a polymeric drug release layer comprising the block copolymer and the therapeutic agent disposed over and in contact with the adhesion promoting layer.

An advantage of the present invention is medical devices are provided with therapeutic-agent-releasing layers which have improved adhesion to metallic substrates.

These and many other aspects, embodiments and advantages of the present invention will become immediately apparent to those of ordinary skill in the art upon review of the Detailed Description and Claims to follow.

BRIEF DESCRIPTION OF THE DRAWINGS

FIGS. 2A-2C are schematic cross-sectional views of stent struts in accordance with various embodiments of the present invention.

FIGS. 3A-3C are schematic cross-sectional views of stent struts in accordance with various further embodiments of the present invention.

DETAILED DESCRIPTION OF THE INVENTION

Figure 1A:
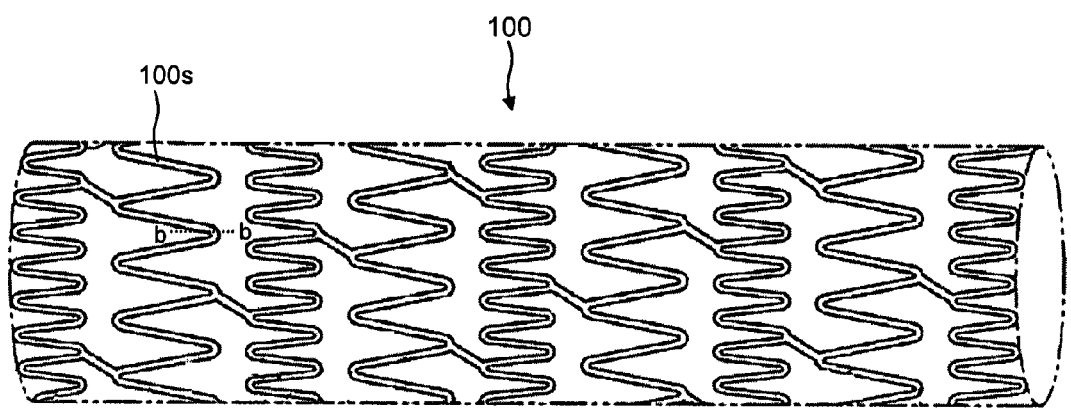
FIG. 1A is a schematic perspective view of a stent in accordance with the prior art.
Figure 1B:
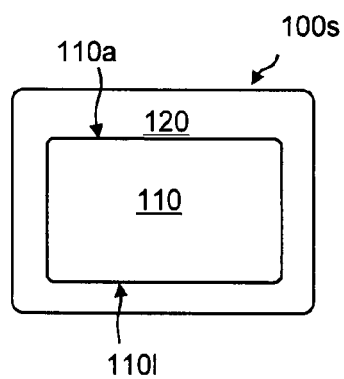
FIG. 1B is a schematic cross-sectional view of the stent of FIG. 1A, taken along line b-b.

A more complete understanding of the present invention is available by reference to the following detailed description of numerous aspects and embodiments of the invention. The detailed description of the invention which follows is intended to illustrate but not limit the invention.

According to an aspect of the present invention, a medical device is provided which comprises a metallic substrate and polymeric region disposed over and in contact with the metallic substrate. The polymeric region comprises (a) a block copolymer that comprises (i) a hard polymer block that comprises a high Tg monomer and (ii) a soft polymer block that comprises a low Tg monomer, (b) an adhesion promoting copolymer that comprises (i) a first monomer that covalently or non-covalently bonds with the metallic substrate and (ii) a second monomer that is compatible with the low Tg monomer and/or the high Tg monomer and (c) a therapeutic agent. The polymeric region may further comprise an optional release-affecting polymer that is used to tailor the release profile of the therapeutic agent, for example, so that an optimal dose profile is obtained as ascertained by clinical results. Such an optional release-affecting polymer may be, for example, a copolymer that comprises (i) a monomer that is compatible with one of the high and low Tg monomers of the block copolymer and (ii) a monomer that is incompatible with the other of the high and low Tg monomers of the block copolymer.

As used herein, a "polymeric region" is a three-dimensional entity that contains polymers, for example, from 50 wt % or less to 75 wt % to 90 wt % to 95 wt % to 97.5 wt % to 99 wt % or more polymers. As used herein, polymeric regions can comprise two or more adjacent polymeric layers.

As used herein, a "polymeric layer" is a layer that contains polymers. Layers in accordance with the present invention can be disposed over all or only a portion of the underlying metallic substrate, depending on the application. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate.

As used herein, an "adhesion promoting layer" is a polymeric layer that, when disposed between a metallic substrate and an additional polymeric layer, provides improved adhesion of the additional polymeric layer to the metallic substrate, relative to such adhesion in the absence of the adhesion promoting layer.

As used herein, an "adhesion promoting copolymer" is (a) a copolymer that, when included in a polymeric layer with one or more other polymers, provides improved adhesion of the polymeric layer to an adjacent metallic substrate, relative to such adhesion when the adhesion promoting polymer is not included in the polymeric layer or (b) a copolymer that, when disposed in a first polymeric layer between a metallic substrate and a second polymeric layer, provides improved adhesion of the second polymeric layer to the metallic substrate, relative to such adhesion in the absence of the first polymeric layer.

Adhesion may be measured, for example, by ASTM Test Method D1876-01 Standard Test Method for Peel Resistance of Adhesives (T-Peel Test) or similar test methods or by measuring 180 degree peel of the coating from the substrate (similar to ASTM peel adhesion 3330/D3330M-04).

As used herein, a "polymeric drug release layer" is a polymeric layer that contains a therapeutic agent, at least a portion of which is released from the polymeric drug release layer in vivo.

As used herein a "metallic substrate" is one containing metals, for example, from 50 wt % or less to 75 wt % to 90 wt % to 95 wt % to 97.5 wt % to 99 wt % or more metals. These include pure metallic substrates (excluding impurities, native and non-native oxides, etc.) such as those formed from pure single metals (e.g. Ti, Ta), and pure metal alloys, for example, alloys comprising iron and chromium (e.g., stainless steels, including platinum-enriched radiopaque stainless steel), niobium alloys, titanium alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys).

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used.

As used herein a first monomer is "compatible" with a second monomer where the first monomer is the same as the second monomer, or wherein polymers of the first and second monomers are miscible with each other.

Polymers may take on a number of configurations, which may be selected, for example, from linear, branched and cyclic configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" or "block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear block.

Medical devices in accordance with the invention vary widely. Examples include implantable or insertable medical devices, for example, catheters (e.g., renal or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, embolization devices including cerebral aneurysm filler coils (including Gugliemi detachable coils and metal coils), embolic agents, septal defect closure devices, myocardial plugs, patches, pacemakers, pacemaker leads, defibrillation leads and coils, ventricular assist devices including left ventricular assist hearts and pumps, total artificial hearts, shunts, valves including heart valves and vascular valves, anastomosis clips and rings, cochlear implants, tissue bulking devices, suture anchors, tissue staples, ligating clips at surgical sites, cannulae, metal wire ligatures, urethral slings, hernia "meshes", orthopedic prosthesis such as bone grafts, bone plates, fins and fusion devices, and tissue engineering scaffolds for cartilage, bone, skin and other in vivo tissue regeneration, biopsy devices, as well as any other device that is implanted or inserted into the body and from which therapeutic agent is released.

According to an embodiment of the invention, medical devices are provided which include (a) a metallic substrate and (b) a polymeric drug release layer disposed over and in contact with the metallic substrate containing (e.g., in the form of a blend or other admixture) (i) a block copolymer, (ii) an adhesion promoting copolymer and (iii) a therapeutic agent. As noted above, the block copolymer includes (i) a hard polymer block that includes a high Tg monomer and (ii) a soft polymer block that includes a low Tg monomer, whereas the adhesion promoting copolymer includes (i) a monomer that covalently or non-covalently bonds with the metallic substrate and (ii) a monomer that is compatible with the low Tg monomer and/or the high Tg monomer, or a monomer that is compatible with the low Tg monomer in combination with a different monomer that is compatible with the high Tg monomer. As also noted above, the polymeric region may further comprise an optional release-affecting polymer. Such an optional release-affecting polymer may be, for example, a copolymer that comprises (i) a monomer that is compatible with one of the high and low Tg monomers of the block copolymer and (ii) a monomer that is incompatible with the other of the high and low Tg monomers of the block copolymer.

Without wishing to be bound by theory, it is believed that the monomer within the adhesion promoting copolymer that covalently or non-covalently bonds with the metallic substrate promotes good adhesion of the polymeric drug release layer to the substrate, whereas the monomer(s) within the adhesion promoting copolymer that is(are) compatible with the low Tg and/or high Tg monomers of the block copolymer promote(s) good interaction between the adhesion promoting copolymer and the block copolymer within the polymeric drug release layer.

A specific embodiment of this aspect of the invention is illustrated in FIG. 2A, which is a cross-sectional view of a stent strut 110s, for example, one corresponding to a stent design like that of FIG. 1A (except for the coating scheme, as described below). The stent strut 110s includes a metallic stent substrate 110 over which is disposed a polymeric region, in particular, an adhesion promoting polymeric drug release layer 210 that contains (i) a block copolymer, (ii) an adhesion promoting polymer, (iii) a therapeutic agent and (iv) an optional release-affecting polymer.

Another specific embodiment is illustrated in FIG. 2B, which like FIG. 2A is a cross-sectional view of a stent strut 110s that includes a metallic stent substrate 110 over which is disposed an adhesion promoting, polymeric drug release layer 210 containing (i) a block copolymer, (ii) an adhesion promoting polymer, (iii) a therapeutic agent and (iv) an optional release-affecting polymer. Unlike FIG. 2A, however, the polymeric drug release layer in FIG. 2B is applied only to the abluminal surface 110a of the stent substrate 110 in this embodiment. Such a layer 210 may be created, for example, by coating a tubular stent precursor (e.g., a tube) with the polymeric drug release layer 210 prior to removing material (e.g., by cutting, punching, etc.) in order to form the apertures (and thus the struts) of the stent, or by any other suitable methodology (e.g., transfer coating).

Yet another specific embodiment is illustrated in FIG. 2C, which, like FIGS. 2A and 2B, is a cross-sectional view of a stent strut 110s that includes a metallic stent substrate 110 over which is disposed an adhesion promoting, polymeric drug release layer 210 containing (i) a block copolymer, (ii) an adhesion promoting polymer, (iii) a therapeutic agent and (iv) an optional release-affecting polymer. Unlike FIGS. 2A and 2B, however, the polymeric drug release layer in FIG. 2C is applied to the abluminal surface 110a of the stent substrate 110, as well as to the sides of the stent substrate 110 between the abluminal surface 110a and the luminal surface 110l. Such a layer 210 may be created, for example, by masking the inner luminal surface of the stent 110l during deposition of the polymeric drug release layer 210, by removing polymeric material from the inner luminal surface of the stent 110l after creating the polymeric drug release layer 210, or by any other suitable methodology.

The embodiments of FIGS. 2B and 2C are more demanding from an adhesion standpoint than the embodiment of FIG. 2A, because the coating does not surround the stent substrate 110 as it does in FIG. 2A. Thus, the present invention is particularly advantageous in such embodiments.

According to another embodiment of the invention, medical devices are provided which include (a) a metallic substrate, (b) an adhesion promoting layer containing an adhesion promoting copolymer disposed over and in contact with the metallic substrate, and (c) a polymeric drug release layer containing (e.g., in the form of a blend or other admixture) a block copolymer, a therapeutic agent and an optional release-affecting polymer disposed over and in contact with the adhesion promoting layer.

As noted above, the block copolymer includes (i) a hard polymer block that includes a high Tg monomer and (ii) a soft polymer block that includes a low Tg monomer. The adhesion promoting copolymer includes (i) a monomer that covalently or non-covalently bonds with the metallic substrate and (ii) a monomer that is compatible with the low Tg monomer and/or a monomer that is compatible with the high Tg monomer, or a monomer that is compatible with the low Tg monomer in combination with a different monomer that is compatible with the high Tg monomer. The optional release-affecting polymer may be, for example, a copolymer that comprises (i) a monomer that is compatible with one of the high and low Tg monomers of the block copolymer and (ii) a monomer that is incompatible with the other of the high and low Tg monomers of the block copolymer.

Without wishing to be bound by theory, it is believed that the monomer within the adhesion promoting copolymer that covalently or non-covalently bonds with the metallic substrate promotes good adhesion of the adhesion promoting layer to the underlying substrate, whereas the monomer(s) within the adhesion promoting copolymer that is(are) compatible with the low Tg and/or high Tg monomers of the block copolymer promote(s) good interaction between the adhesion promoting layer and the overlying polymeric drug release layer.

A specific embodiment of this aspect of the invention is illustrated in FIG. 3A, which is a cross-sectional view of a stent strut 110s, for example, one corresponding to a stent design like that of FIG. 1A (except for the coating scheme as described below). The stent strut 110s of FIG. 3A includes a metallic stent substrate 110 and a polymeric region 300 that includes an adhesion promoting layer 320 that contains an adhesion promoting copolymer and is disposed over and in contact with the metallic stent substrate 110 as well as a polymeric drug release layer 330 that contains a block copolymer, a therapeutic agent and an optional release-affecting polymer, disposed over and in contact with the adhesion promoting layer 320.

Another specific embodiment is illustrated in FIG. 3B, which is a cross-sectional view of a stent strut 110s that includes a stent substrate 110 and a polymeric region 300. The polymeric region 300 further includes an adhesion promoting layer 320, which contains an adhesion promoting copolymer and is disposed over and in contact with the stent substrate 110, and a polymeric drug release layer 330, which contains a block copolymer, a therapeutic agent and an optional release-affecting polymer, disposed over and in contact with the adhesion promoting layer 320. Unlike FIG. 3A, the adhesion promoting layer 320 and the polymeric drug release layer 330 of FIG. 3B are applied to only the abluminal surface 110a of the stent substrate 110 in this embodiment. Such a structure may be created, for example, by coating a tubular stent precursor with the adhesion promoting layer 320 and the polymeric drug release layer 330 prior to removing material (e.g., by cutting, punching, etc.) to form the apertures (and thus the struts) of the stent, or by any other suitable methodology (e.g., transfer coating).

Yet another specific embodiment is illustrated in FIG. 3C, which is a cross-sectional view of a stent strut 110s that includes a stent substrate 110 and a polymeric region 300. The polymeric region 300 further includes an adhesion promoting layer 320, which contains an adhesion promoting copolymer and is disposed over and in contact with the stent substrate 110, and a polymeric drug release layer 330, which contains a block copolymer, a therapeutic agent and an optional release-affecting polymer, disposed over and in contact with the adhesion promoting layer 320. Unlike FIGS. 3A and 3B, the adhesion promoting layer 320 and the polymeric drug release layer 330 are applied to the abluminal surface 110a of the stent substrate 110, as well as to the sides of the stent substrate 110 between the abluminal surface 110a and the luminal surface 110l. Such a structure may be created, for example, by masking the inner luminal surface of the stent 110l during deposition of the adhesion promoting layer 320 and the polymeric drug release layer 330, by removing polymeric material from the inner luminal surface of the stent 110l after deposition of the adhesion promoting layer 320 and the polymeric drug release layer 330, or by any other suitable methodology.

The embodiments of FIGS. 3B and 3C are more demanding from an adhesion standpoint than the embodiment of FIG. 3A, because the coating does not surround the stent substrate 110 as it does in FIG. 3A.

As indicated above, medical devices in accordance with the present invention contain (in addition to an adhesion promoting copolymer and an optional release-affecting polymer) one or more types of block copolymers that contain (a) one or more hard polymer blocks, which include one or more types of high Tg monomers, and (b) one or more soft polymer blocks, which include one or more types of low Tg monomers.

As used herein, a "soft polymer block," also referred to as a "low Tg polymer block," is one that displays a Tg that is below body temperature, more typically from 35° C. to 20° C. to 0° C. to −25° C. to −50° C. or below. A low Tg monomer is one that displays a Tg that is below body temperature when formed into a homopolymer. Conversely, as used herein, a "hard polymer block," also referred to as a "high Tg polymer block," is one that displays a Tg that is above body temperature, more typically from 40° C. to 50° C. to 75° C. to 100° C. or above. A high Tg monomer is one that displays a Tg that is above body temperature when formed into a homopolymer. Tg can be measured by differential scanning calorimetry (DSC).

Specific examples of low Tg polymer blocks include homopolymer and copolymer blocks containing one or more of the following low Tg monomers (listed along with published Tg's for homopolymers of the same): (1) unsubstituted and substituted alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, and halogenated alkene monomers including vinylidene chloride (Tg −18° C.), vinylidene fluoride (Tg −40° C.), cis-chlorobutadiene (Tg −20° C.), and trans-chlorobutadiene (Tg −40° C.); (2) acrylic monomers including: (a) alkyl acrylates such as methyl acrylate (Tg 10° C.), ethyl acrylate (Tg −24° C.), propyl acrylate, isopropyl acrylate (Tg −11° C., isotactic), n-butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers including tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); and (7) siloxane monomers including dimethylsiloxane (Tg −127° C.), diethylsiloxane, methylethylsiloxane, methylphenylsiloxane (Tg −86° C.), and diphenylsiloxane.

Specific examples of high Tg polymer blocks include homopolymer and copolymer blocks containing one or more of the following high Tg monomers: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, unsubstituted and substituted vinyl pyridines such as 2-vinyl pyridine (Tg 104° C.) and 4-vinyl pyridine (Tg 142° C.), and other vinyl aromatic monomers such as vinyl carbazole (Tg 227° C.) and vinyl ferrocene (Tg 189° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines, (c) vinyl halides such as vinyl chloride (Tg 81° C.) and vinyl fluoride (Tg 40° C.), (d) alkyl vinyl ethers such as tert-butyl vinyl ether (Tg 88° C.) and cyclohexyl vinyl ether (Tg 81° C.), and (e) other vinyl compounds such as vinyl pyrrolidone; (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

As used herein, a poly(vinyl aromatic) block is a polymer block that contains multiple copies of one or more types of vinyl aromatic monomers, a polyalkene block is a block that contains multiple copies of one or more types of alkene monomers, a polyacrylate block is a block that contains multiple copies of one or more types of acrylate monomers, a polymethacrylate block is a block that contains multiple copies of one or more types of methacrylate monomers, a polysiloxane block is a block that contains multiple copies of one or more types of siloxane monomers, and so forth.

A few examples of block copolymer structures that may be formed from hard blocks ("H") and soft blocks ("S") include the following, among others: (a) block copolymers having alternating blocks of the type $(HS)_m$, $S(HS)_m$ and $H(SH)_m$ where, m is a positive whole number of 1 or more, and (b) block copolymers having multi-arm geometries, such as $X(SH)_n$, and $X(HS)_n$, where n is a positive whole number of 2 or more and X is a hub species (e.g., an initiator molecule residue, a residue of a molecule to which preformed polymer chains are attached, etc.). In addition to the hub species mentioned above, copolymers such as those above can contain a variety of other non-polymer-chain species, which are commonly present in copolymers, including capping molecules, among others. Note that non-polymer species, such as hub species, linking species, etc. are generally ignored in describing block copolymer morphology, for example, with $X(SH)_2$ being designated as an HSH triblock copolymer. Other examples of block copolymers include comb copolymers having an S chain backbone and multiple H side chains, as well as comb copolymers having an H chain backbone and multiple S side chains.

As seen from the above, in certain other embodiments, the block copolymer employed is a diblock copolymer that contains a single low Tg block and a single high Tg block, in certain other embodiments of the invention, the block copolymer employed comprises a low Tg block and at least two high Tg blocks, with at least a portion of the low Tg block separating the high Tg blocks (in other words the high Tg blocks are interconnected via the low Tg block), and so forth. Polymers of the latter type are capable of demonstrating high strength and elastomeric properties, while at the same time being processable using techniques such as solvent- and/or melt-based processing techniques. As is well known, block copolymers tend to phase separate. In the polymers like those described above, the high Tg blocks (which are hard) will aggregate to form hard phase domains. Without wishing to be bound by theory, it is believed that because the high Tg hard blocks are interconnected via low Tg blocks (or portions thereof, e.g., in the case of a graft copolymer), which low Tg blocks or portions thereof are elastomeric, the hard phase domains become physically crosslinked to one another via the elastomeric blocks. Moreover, because the crosslinks are not covalent in nature, they can be reversed, for example, by dissolving or melting the block copolymer.

In addition to one or more types of block copolymers, each including (i) at least one hard polymer block that include at least one type of high Tg monomer and (ii) at least one soft polymer block that include at least one type of low Tg monomer and in addition to one or more types of optional release-affecting polymers, the medical devices of the present invention also employ at least one adhesion promoting copolymer. Adhesion promoting copolymers in accordance with the invention include the following (a) copolymers that include at least one monomer that covalently or non-covalently bonds with a metallic substrate and at least one monomer that is compatible with the at least one low Tg monomer within the block copolymer (i.e., the same monomer or a different monomer with high affinity to the low Tg monomer, for instance, where homopolymers of the low Tg monomer and the differing monomer are miscible with each other), (b) copolymers that include at least one monomer that covalently or non-covalently bond with a metallic substrate and at least one monomer that is compatible with the at least one high Tg monomer within the block copolymer (e.g., the same monomer or a different monomer with high affinity to the high Tg monomer), and (c) copolymers that include at least one monomer that covalently or non-covalently bond with a metallic substrate, at least one monomer that is compatible with the at least one low Tg monomer within the block copolymer, and at least one monomer that is compatible with the at least one high Tg monomer within the block copolymer.

Without wishing to be bound by theory, it is known that water has a strong propensity to wet out metals such as stainless steel, which frequently results in the displacement of polymeric layers that are disposed on such surfaces. However, this propensity may be combated in accordance with the invention by providing adhesion promoting polymers that form covalent or strong non-covalent bonds (e.g., strong acid-base interactions) with the metal surface.

Examples of monomers that are capable of covalently bonding to metallic substrates include those containing one or more alkoxysilane groups, for example, those containing

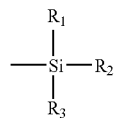

groups, for example,

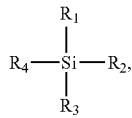

where $R_1$, $R_2$ and $R_3$ are independently alkyl (e.g., linear or branched $C_1$-$C_{10}$ alkyl such as methyl, ethyl, n-propyl, isopropyl, n-butyl, sec-butyl, iso-butyl, tert-butyl, n-pentyl, etc.), aryl (e.g., $C_6$-$C_{12}$ aryl such as phenyl, alkyl-substituted phenyl, etc.) or alkoxy (e.g., linear or branched $C_1$-$C_{10}$ alkoxy such as methoxy, ethoxy, n-propoxy, isopropoxy, n-butoxy, sec-butoxy, iso-butoxy, tert-butoxy, etc.) groups, with the proviso that at least one of $R_1$, $R_2$, $R_3$ is an alkoxy group, and where $R_4$ contains a reactive group which can be polymerized into a polymer chain or backbone (e.g., $R_4$ may be vinyl, acryloyloxy, methacryloyloxy, etc.). Such groups may be present on the monomer at the time of polymerization or may be added to the monomers within the subsequently formed polymer, with the exception of $R_4$, which is incorporated into the polymer at the time of polymerization.

Alkoxysilanes are known to react with metal hydroxides. For example, an alkoxysilane group of an adhesion promoting polymer ("Poly") in accordance with the invention may react with hydroxyl groups on metal surface as schematically illustrated below:

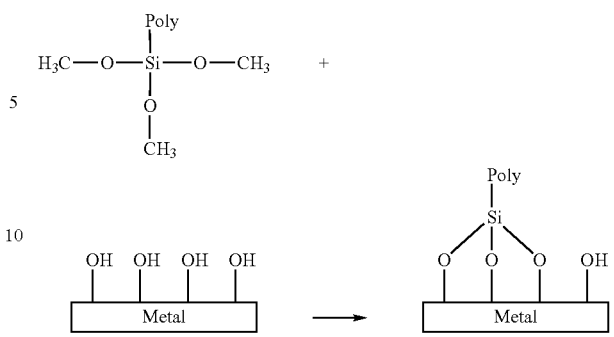

Alkoxysilane groups may also react with themselves to form Si—O—Si bonds.

Specific examples of alkoxysilane monomers include, for example, vinyl(alkylene)alkoxysilanes such as those of the formula

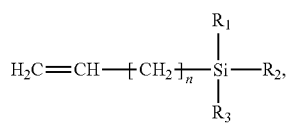

acryloyloxy(alkylene)alkoxysilanes such as those of the formula

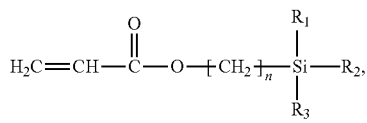

and methacryloyloxy(alkylene)alkoxysilanes such as those of the formula

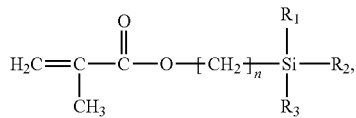

where n=0, 1, 2, 3, 4, 5, 6, 7, 8, 9, etc. and $R_1$, $R_2$ and $R_3$ are defined above, among others. More specific examples of such monomers include vinyltrimethoxysilane, vinyltriethoxysilane, vinyltriisopropoxysilane, vinylmethylenetrimethoxysilane, vinyldimethylenetrimethoxysilane, vinyltrimethylenetrimethoxysilane, (meth)acryloyloxytrimethoxysilane, (meth)acryloyloxytriethoxysilane, (meth)acryloyloxytriisopropoxysilane, (meth)acryloyloxymethylenetrimethoxysilane, (meth)acryloyloxydimethylenetrimethoxysilane, and (meth)acryloyloxytrimethylenetrimethoxysilane, among many others.

Examples of monomers that are capable of forming strong non-covalent bonds with metallic substrates include monomers with acidic groups, for example, groups that act as Bronsted acids and/or groups that act as Lewis acids. Such groups may be present on the monomers at the time of polymerization, or they may be added to the monomers within the subsequently formed polymer.

A Bronsted acid is a proton (e.g., hydrogen ion) donor, whereas a Bronsted base is a proton (e.g., hydrogen ion) acceptor. A Lewis acid is an electron pair acceptor, whereas a Lewis base is an electron pair donor. Bronsted acids are Lewis acids, but the converse is not always true. Also, Bronsted bases are Lewis bases, although the converse is not necessarily true.

Without wishing to be bound by theory, it is believed that because metallic surfaces are typically basic in nature, polymers with acidic groups are able to form strong acid-base interactions with metallic surfaces. For example, an acid-base reaction can occur upon exposure of metallic surfaces to an acid. For instance, a proton may be transferred from the acidic monomer to the metal oxide, or the metal oxide may donate an electron pair to the acidic monomer, among other possibilities.

Specific examples of acidic monomers are those that contain Bronsted acid groups such as carboxylic acid groups (—COOH), carboxylic acid anhydride groups

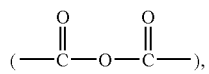

hydroxyl acid groups, for example, hydroxyaromatic groups such as mono- and di-hydroxyphenyl groups, sulfonic acid groups (—SO$_3$H), phosphonic acid groups (—PO(OH)$_2$).

More specific examples of acidic monomers include acrylic acid, methacrylic acid, 2-ethylacrylic acid, 2-propylacrylic acid, 2-(bromomethyl)acrylic acid, 2-(trifluoromethyl)acrylic acid, 2-bromoacrylic acid, 2-(trifluoromethyl) acrylic acid, 2-ethylacrylic acid, methylenemalonic acid, vinylacetic acid, allylacetic acid, styryl acetic acid, 4-vinylbenzoic acid, dimethylacrylic acid, phenylacrylic acid, hydroxystyrene, dihydroxystyrene, maleic anhydride, succinic anhydride, vinylsulfonic acid, 4-styrenesulfonic acid, 3-(vinyloxy)propane-1-sulfonic acid, 2-acrylamido-2-methyl-1-propanesulfonic acid, 3-allyloxy-2-hydroxy-1-propanesulfonic acid, 2-sulfoethyl methacrylate, 2-sulfoethyl acrylate, 3-sulfopropyl acrylate, sulfoethyl methacrylamide, vinylphosphonic acid, and allylphosphonic acid, among others.

In addition to one or more types of block copolymers and one or more types of adhesion promoting copolymers, the medical devices of the present invention also optionally employ one or more release-affecting polymers. Such an optional release-affecting polymer may be, for example, a copolymer that comprises (i) a monomer that is compatible with a low Tg monomer of the block copolymer and (ii) a monomer that is incompatible with a high Tg monomer of the block copolymer. As another example, the optional release-affecting polymer may be a copolymer that comprises (i) a monomer that is compatible with a high Tg monomer of the block copolymer and (ii) a monomer that is incompatible with a low Tg monomer of the block copolymer.

As a specific example, the block copolymer may be a poly(styrene-b-alkene) block copolymer such as SIBS, whereas the optional release-affecting polymer may be a poly(styrene-co-maleic anhydride) copolymer (SMA), which contains styrene monomer (and is thus compatible with the high Tg styrene monomer of the block copolymer) and a maleic anhydride monomer (which is incompatible with the low Tg alkene monomer of the block copolymer). For example, it has been found that SMA increases the release rate of paclitaxel and also decreases the amount of residual paclitaxel that remains in the drug-containing layer. SMA, however, is not a particularly effective adhesion promoter for SIBS. In addition to SIBS and SMA, the polymeric region may further comprise an adhesion promoting copolymer that comprises maleic anhydride, such that there is compatibility between the maleic anhydride in the SMA and the maleic anhydride in the adhesion promoting copolymer.

As will be appreciated by those of ordinary skill in the art, the copolymers employed in accordance with the present invention, including various block copolymers, adhesion promoting copolymers and optional release-affecting polymers, may be synthesized according to known methods, including cationic, anionic, and radical polymerization methods, particularly controlled/"living" cationic, anionic and radical polymerizations.

Living free radical polymerizations (also called controlled free radical polymerizations) may be employed in various embodiments, due to the undemanding nature of radical polymerizations in combination with the power to control polydispersities, architectures, and molecular weights that living processes provide. Monomers capable of free radical polymerization vary widely and may be selected from the following, among many others: vinyl aromatic monomers such as substituted and unsubstituted styrene, diene monomers such as 1,3-butadiene, chloroprene, and isoprene, acrylate monomers, for example, acrylate esters such as butyl acrylate and methyl acrylate, methacrylate monomers, for example, methacrylic esters such as methyl methacrylate, beta-hydroxyethyl methacrylate, and beta-dimethylaminoethyl methacrylate, as well as other unsaturated monomers including acrylic acid, acrylamide, acrylonitrile, ethylene, propylene, tetrafluoroethylene, triflourochloroethylene, iraconic acid, fumaric acid, maleic acid, methacrylic acid, methacrylonitrile, vinyl esters such as vinyl acetate, vinyl chloride, vinyl fluoride, N-vinylpyrrolidinone, N-vinylimidazole, vinylidene chloride, and vinylidene fluoride, among many others.

Specific examples of free radical polymerization processes include metal-catalyzed atom transfer radical polymerization (ATRP), stable free-radical polymerization (SFRP), including nitroxide-mediated processes (NMP), and degenerative transfer including reversible addition-fragmentation chain transfer (RAFT) processes. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), B. Reeves, "Recent Advances in Living Free Radical Polymerization," Nov. 20, 2001. University of Florida, T. Kowalewski et al., "Complex nanostructured materials from segmented copolymers prepared by ATRP," *Eur. Phys. J. E,* 10, 5-16 (2003).

ATRP is an appealing free radical polymerization technique, as it is tolerant of a variety of functional groups (e.g., alcohol, amine, and sulfonate groups, among others) and thus allows for the polymerization of many monomers. In monomer polymerization via ATRP, radicals are commonly generated using organic halide initiators and transition-metal complexes. Some typical examples of organic halide initiators include alkyl halides, haloesters (e.g., methyl 2-bromopropionate, ethyl 2-bromoisobutyrate, etc.) and benzyl halides (e.g., 1-phenylethyl bromide, benzyl bromide, etc.). A wide range of transition-metal complexes may be employed, including a variety of Ru-, Cu-, Os- and Fe-based systems. Examples of monomers that may be used in ATRP polymerization reactions include various unsaturated monomers such as alkyl acrylates, alkyl methacrylates, hydroxyalkyl methacrylates, vinyl esters, vinyl aromatic monomers, acrylamide, methacrylamide, acrylonitrile, and 4-vinylpyridine, among others. In ATRP, at the end of the polymerization, the polymer chains are capped with a halogen atom that can be readily transformed via $S_N1$, $S_N2$ or radical chemistry to provide other functional groups such as amino groups, among many others. Functionality can also be introduced into the polymer by other methods, for example, by employing initiators that contain functional groups which do not participate in the radical polymerization process. Examples include initiators with epoxide, azido, amino, hydroxyl, cyano, and allyl groups, among others. In addition, functional groups may be present on the monomers themselves.

Radical polymerizations based upon degenerative transfer systems generally employ transfer agents that contain moieties for both initiation and transfer, which are generated in the presence of radicals. Controlled radical polymerizations from degenerative transfer reactions have been performed with alkyl iodides, unsaturated methacrylate esters and thioesters as the transfer agents, among others. The use of thioesters in the radical polymerization of vinyl monomers results in a RAFT polymerization. The RAFT process has proven to be a versatile method, capable of polymerizing an extremely broad range of radical polymerizable monomers, including functional styrenes, (meth)acrylates, and vinyl esters, as well as water soluble monomers including ionic species such as sodium 2-acrylamido-2-methylpropanesulfonate (AMPS) and sodium 3-acrylamido-3-methylbutanoate (AMBA), among many others. Thio endgroups remaining after RAFT may be removed or displaced by other groups via radical chemistry.

SFRP polymerizations, including NMP, utilize alkoxyamine initiators and nitroxide persistent radicals to polymerize monomers such as styrenes and acrylates. A widely used nitroxide in the polymerization of styrene is 2,2,6,6-tetramethylpiperidinyloxy (TEMPO), although more recently developed nitroxides can also polymerize acrylates, acrylamides, 1,3-dienes and acrylonitrile based monomers, among others, in a controlled fashion. The resulting polymers contain terminal alkoxyamine groups, which may be transformed with radical chemistry. For example, maleic anhydride or maleimide derivatives may be added to the alkoxyamine, allowing the ready introduction of other functional groups.

As noted above, polymeric drug release layers in accordance with the present invention further contain at least one therapeutic agent. "Therapeutic agents," "drugs," "pharmaceutically active agents," "pharmaceutically active materials," "active pharmaceutical ingredients" (API's) and other related terms may be used interchangeably herein.

The rate of release of therapeutic agents from the polymeric drug release layers of the invention will depend, for example, on nature of the therapeutic agents within the drug release layers, the nature of the block copolymers within the drug release layer (e.g., molecular weight, architecture, and monomer composition), and the nature of any other optional supplemental species, including any release-affecting polymers and/or adhesion promoting copolymer that is present within the drug release layers. For instance, the nature of the therapeutic agents (e.g., hydrophilic/hydrophobic) and the nature of the monomers (e.g., hydrophilic/hydrophobic/swellable) within the polymer(s) will have a significant effect upon the release of the drug (affecting, for example, the wettability of the polymeric layers, the water diffusivity, the therapeutic agent diffusivity, and so forth).

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin(sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Several preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

A wide range of therapeutic agent loadings may be used in conjunction with the medical devices of the present invention. Typical loadings range, for example, from than 1 wt % or less to 2 wt % to 5 wt % to 10 wt % to 25 wt % or more of the polymeric region.

Numerous techniques are available for forming polymeric drug release layers and adhesion promoting layers in accordance with the present invention.

For example, where a layer is formed from one or more polymers having thermoplastic characteristics, a variety of standard thermoplastic processing techniques may be used. Using these techniques, a layer can be formed, for instance, by (a) first providing a melt that contains polymer(s) as well as other desired agents such as therapeutic agent(s) and any optional supplemental non-polymeric agents and (b) subsequently cooling the melt.

Other processing techniques besides thermoplastic processing techniques may also be used to form layers, including solvent-based techniques. Using these techniques, a polymeric layer can be formed, for instance, by (a) first providing a solution or dispersion that contains polymer(s) as well as other desired agents such as therapeutic agent(s) and any optional supplemental non-polymeric agents and (b) subsequently removing the solvent. The solvent that is ultimately selected will contain one or more solvent species, which are generally selected based on their ability to dissolve or disperse the various species making up the layer (e.g., one or more polymers, one or more therapeutic agents, one or more optional agents, etc.), in addition to other factors, including drying rate, surface tension, etc.

Preferred thermoplastic and solvent-based techniques include, for example, spraying techniques, dipping techniques, spin coating techniques, web coating techniques, meniscus coating techniques, gravure or other transfer coating techniques, knife or blade coating, techniques involving coating via mechanical suspension including air suspension, ink jet techniques, electrostatic techniques, and combinations of these processes.

Several specific embodiments of the invention will now be described in the Examples to follow. These examples should not be construed as limiting. Other examples can be envisioned by those of ordinary skill in the art.

Example 1

Poly(methyl methacrylate-b-butyl acrylate-b-methyl methacrylate) triblock copolymer (MBAM) is desirable from a drug release standpoint as it undergoes essentially 100% release of therapeutic agent in vivo, even of highly hydrophobic agents such as paclitaxel. Also, because the copolymer contains two hard blocks interconnected by a soft elastic block, reversible physical crosslinks are typically formed during processing, resulting in a copolymer with good strength. Moreover, because MBAM is a copolymer, one can tailor the drug release and mechanical properties of the copolymer by varying the ratio of methyl methacrylate (MMA) to butyl acrylate (BA) within the polymer, among other variations (e.g., variations in architecture, molecular weight, etc.). For example, with respect to mechanical properties, MMA is brittle, whereas BA is tacky, allowing the relative proportions of these monomers to be adjusted to achieve a non-brittle, non-sticky copolymer.

As noted above, for vascular stent applications, it may be desirable that only the abluminal surface of the stent be coated. This requires excellent adhesion, since one cannot rely upon encapsulation of the stent by the coating to hold the coating onto the stent. However, MBAM has relatively poor adhesion, and it can be easily peeled from metals such as stainless steel. To improve the adhesion of MBAM to metals, the following random copolymers of MMA, BA and either acrylic acid (AA) or maleic anhydride (MA) were formed, each in the following weight ratios: 49/46/5 MMA/BA/AA (theoretical Tg=10° C.), 72/23/5 MMA/BA/AA (theoretical Tg=50° C.), 45/45/10 MMA/BA/AA, 67/23/10 MMA/BA/AA, and 49/46/5 MMA/BA/MA.

MMA/BA/AA and MMA/BA/MA copolymers were synthesized by free radical polymerization in refluxing toluene using benzoyl peroxide as the initiator. The monomers and initiator were combined and slowly added (over 3 hr) to refluxing toluene under a nitrogen atmosphere. After addition of the monomers the reaction was allowed to proceed for an additional 3 hrs. The polymer solution was precipitated into heptane, filtered and dried under vacuum.

It is believed that the carboxylic acid groups of the AA and the anhydride groups of the MA are capable of forming a strong acid-base interaction with metals such as stainless steel. This strong specific interaction results in enhanced adhesion. The MMA and BA, on the other hand, provide compatibility with MBAM. As with the MBAM, various mechanical properties of the MMA/BA/AA copolymers can be varied by varying the monomer content of the copolymer. Also, other acrylic monomers such as ethyl acrylate, ethyl methacrylate, 2-ethyhexyl acrylate and/or 2-ethylhexylmethacrylate may be added to the MMA and BA (or substituted for the MMA or BA) to optimize the mechanical properties of the polymer. In preferred embodiments, however, at least one monomer of the block copolymer is present in the adhesion promoting copolymer (e.g., MMA, BA or both MMA and BA are present). The adhesive monomers in the adhesion promoting copolymer can be optimized as well. For example, AA provides good adhesion when included in the copolymer at low molar amounts (e.g., 5 mol %), but at higher mol % values (e.g., 10 mol %), wet adhesion is seen to suffer. Also, one can get swelling in water at higher mol % values, with the copolymer eventually becoming water dispersible. An increase in AA can also result in a concurrent decrease in solubility of the adhesion promoting copolymer in organic solutions.

Example 2

This example comprises an approach in which the adhesion promoting polymer is deposited in a separate layer from the block copolymer layer. A 10% wt % solution in THF of each acrylic adhesion promoter of Example 1 was knife coated onto stainless steel foil and dried at 70° C. Thickness of the resulting adhesion promoting layer was <1 µm. 25% wt % MBAM (42 wt % BA content) in THF was coated over the adhesion promoting layer via a knife coating technique and dried at 70° C. for 1 hr. The MBAM was purchased from Arkema, Inc., Philadelphia, Pa., USA. The dry coating thickness was about 60 µm.

Adhesion was determined by peeling the MBAM coating from the foil (180° peel angle) utilizing a tensile tester. The MBAM layer is coated beyond the adhesion promoting layer so that part of the MBAM coating is directly disposed on the stainless steel. This allows one to readily start the peel process from the stainless steel. During the peel test, the peel front eventually reaches the adhesion promoting layer, at which point one measures the adhesion of the adhesion promoting layer. Dry adhesion was performed in air. Wet adhesion was determined after incubation of the coated samples in phosphate buffered saline (PBS) with Tween surfactant (pH 7.4, 0.05% wt/vol Tween 20) at 37° C. for 4 days, and for 30 days. The samples were removed from the incubation bath and transferred to a water bath. 180 degree peel adhesion of the submersed samples was then measured. Results are presented in Table 1 to follow.

TABLE 1

| Top Coat | Adhesion Promoting Copolymer | Dry Adhesion (g/in) | Wet adhesion (4 day) (g/in) | Wet adhesion (30 day) (g/in) | Failure Mode |
| --- | --- | --- | --- | --- | --- |
| MBAM | NONE | 12-20 | 0 g | 0 g | Adhesive |
| MBAM | 49/46/5 MMA/BA/AA | >1400 | >1400 | >1400 | Tensile break of MBAM |
| MBAM | 72/23/5 MMA/BA/AA | 504 | 672 | 749 | Adhesive |
| MBAM | 45/45/10 MMA/BA/AA | >1400 | 550 | 12 | Tensile break (dry) Adhesive (wet) |
| MBAM | 67/23/10 MMA/BA/AA | 761 | 910 | 12 | Adhesive |
| MBAM | 49/46/5 MMA/BA/MA | >1400 | 59 | 54 | Tensile break (dry) Adhesive (wet) |

All adhesion promoting layers significantly improved adhesion of MBAM to stainless steel. In some cases, when the peel process reached the adhesion promoting layer, the coating did not peel away from the stainless steel, but rather elongated and broke when its tensile break point (tensile strength) was reached (cohesive failure of the coating). In these cases, the adhesion strength was greater than the tensile strength of the coating, and the actual adhesion strength may have been significantly greater than the value reported in the table above. Although the MA based adhesion promoting layer improves dry adhesion, wet adhesion at 4 days is less than that observed with each of the AA based adhesion promoting layers, and wet adhesion at 30 days is less than that observed with the 5% AA based adhesion promoting layers, but not the 10% AA based layers.

Example 3

This example comprises an approach in which the adhesion promoting polymer is blended in a single layer with the block copolymer layer. Each acrylic acid adhesion promoting copolymer of Example 1 was blended with MBAM at 10 wt % and 20 wt % adhesion promoting copolymer loading. Coatings were cast at 25% wt % solids, dried and peel tested as described in the previous Example 2. The results are presented in Table 2.

TABLE 2

| Adhesion Promoting Copolymer (MMA/BA/AA) | MBAM/Copolymer Ratio (wt/wt) | Dry Adhesion (g/in) | Wet adhesion (4 day) (g/in) | Wet adhesion (30 day) (g/in) | Failure Mode |
|---|---|---|---|---|---|
| 72/23/5 | 90/10 | 991 | 640 | 685 | adhesive |
| 67/23/10 | 90/10 | 655 | 569 | 660 | adhesive |
| 49/46/5 | 90/10 | 1605 | 1534 | 1325 | adhesive |
| 45/45/10 | 90/10 | 1310 | 1199 | 991 | adhesive |
| 72/23/5 | 80/20 | 584 | 711 | 615 | adhesive |
| 67/23/10 | 80/20 | 584 | 543 | 630 | adhesive |
| 49/46/5 | 80/20 | 1442 | 1321 | 1062 | adhesive |
| 45/45/10 | 80/20 | 1229 | 1285 | 1082 | adhesive |
| None | 100/0 | 34 | 0 | 0 | adhesive |

All adhesion promoting copolymers significantly improved adhesion of MBAM to stainless steel when blended with MBAM.

Example 4

MMA/BA/silane acrylate copolymer (49/46/5 weight ratio) was synthesized by free radical polymerization of MMA, BA and 3-methacryloxypropyltrimethoxysilane (silane acrylate) (from Sigma Aldrich) in refluxing toluene using benzoyl peroxide as the initiator. The monomers and initiator were combined and slowly added (over 3 hr) to refluxing toluene under a nitrogen atmosphere. After addition of the monomer the reaction was allowed to proceed for an additional 3 hrs. The polymer solution was precipitated into heptane, filtered and dried under vacuum.

It is believed that the MMA and BA perform in a manner analogous to their performance in MMA/BA/AA copolymer described above. The silane acrylate, on the other hand, is believed to enhance bonding to stainless steel and other metals by covalently bonding to the metal.

Example 5

This example comprises an approach in which the adhesion promoting polymer is deposited in a separate layer from the block copolymer layer. A 10 wt % solution of the acrylic silane adhesion promoting copolymer of Example 4 is dissolved in toluene, knife coated onto stainless steel foil, and cured at 70° C. for 24 hr. The thickness of the resulting adhesion promoting layer was <1 µm. 25 wt % MBAM in Toluene (42 wt % BA content) was coated over the adhesion promoting layer and dried at 70° C. for 1 hr. The resulting dry coating thickness was about 60 µm. Samples are peel tested as described in the Example 2. The results are presented in Table 3.

TABLE 3

| Adhesion Promoting Copolymer | Dry Adhesion (g/in) | Wet adhesion (4 day) (g/in) | Wet adhesion (30 day) (g/in) | Failure Mode |
|---|---|---|---|---|
| None | 34 | 0 | 0 | Adhesive |
| MMA/BA/silane acrylate | 1370 | 2087 | 2119 | Tensile break |

As seen from the above table, the MBAM dry adhesion is poor and wet adhesion is essentially zero. The two layer composition with MMA/BA/silane acrylate adhesion promoting layer, on the other hand, has excellent dry adhesion (>50× greater than MBAM control). Moreover, this adhesion was not significantly decreased after incubation in PBS for 4 and 30 days

Example 6

This example comprises an approach in which the adhesion promoting polymer is blended in a single layer with the block copolymer layer. A 90 wt %/10 wt % blend of MBAM and the acrylic silane adhesion promoting copolymer of Example 4 was prepared at 25 wt % solids in Toluene. The solution was coated onto stainless steel foil to give a dry coating thickness of about 60 µm. The coating was cured at 70° C. for 24 hr. Samples are peel tested as described in the Example 2. The results are presented in Table 4.

TABLE 4

| Adhesion Promoting Copolymer | MBAM/Copolymer Ratio (wt/wt) | Dry Adhesion (g/in) | Wet adhesion (4 day) (g/in) | Wet adhesion (30 day) (g/in) | Failure Mode |
|---|---|---|---|---|---|
| MMA/BA/silane acrylate | 90/10 | 1423 | 1381 | 1287 | Tensile break |
| None | 100/0 | 34 | 0 | 0 | Adhesive |

As previously noted, MBAM dry adhesion is poor and wet adhesion is essentially zero. By blending in an effective adhesion promoting copolymer, however, dry adhesion is increased dramatically (>50× greater than MBAM control). Moreover, this adhesion was not significantly decreased after incubation in PBS for 4 and 30 days.

Example 7

This example comprises an approach in which the adhesion promoting polymer is deposited in a separate layer from the block copolymer layer. Poly(styrene-b-isobutylene-b-styrene) triblock copolymer (SIBS) was prepared as described in U.S. Pat. No. 6,545,097 to Pinchuk et al. Styrene/maleic anhydride (14 wt % MA) random copolymer (SMA) was obtained from PCI Synthesis, Inc. (formerly PolyCarbon Industries, Inc.), Newburyport, Mass., USA. The SMA is not an effective adhesion promoter. Rather, when provided in a blend with a block copolymer such as SIBS, SMA increases the rate of paclitaxel release and decreases the amount of residual paclitaxel that remains in the blend. Thus, SMA is a release-affecting polymer in accordance with the invention. The adhesion promoting copolymer used in this example is SEBS-g-MA, a poly(styrene-b-ethylene/butylene-b-styrene) triblock copolymer (SEBS) grafted with ~1.5 wt % maleic anhydride (MA), which is available commercially as Kraton® 1901 from Kraton Polymers, Houston, Tex., USA. Kraton® 1901 was coated on stainless steel foil (10 wt % in toluene) and dried at 70° C. for 30 minutes to give a dried coating thickness <1 µm. A blend of SIBS/SMA (70/30 wt/wt) (25 wt % solids in toluene) was coated over the Kraton® layer and dried at 70° C. for 1 hr to yield a coating with ~60 µm dry coating thickness. Adhesion results are show in the following Table 5. One observes a very significant improvement in both dry and wet adhesion compared to the absence of an adhesion promotion layer. The addition of SMA to SIBS does act to modestly increase the adhesion (both dry and wet). SMA, however is not a very effective adhesion promoter, which without wishing to be bound by theory is likely due to the fact that it is not miscible with SIBS (it phase separates from SIBS into a micro-dispersed phase) and hence the maleic anhydride functionality is not uniformly distributed throughout the SIBS matrix.

TABLE 5

| Adhesion Promoting Copolymer | Dry Adhesion (g/in) | Wet adhesion (4 day) (g/in) | Failure Mode |
|---|---|---|---|
| None-SIBS only; no SMA | 232 | 108 | Adhesive |
| None-SIBS/SMA blend only | 383 | 300 | Adhesive |
| Kraton ® 1901-SIBS/SMA blend | 2402 | 2521 | Tensile |

Example 8

Single layer blends of SIBS, SMA and Kraton® (the same as described in Example 7) were also evaluated. Blends (70/30 wt/wt SIBS/SMA containing 10 and 20 wt % Kraton®) were coated from toluene at 25 wt % solids, 20 mil gap on stainless steel foil as previously described (~60 µm dry coating thickness). Adhesion results are show in the following Table 6. One observes a significant improvement in both dry and wet adhesion compared to the absence of an adhesion promoting copolymer.

TABLE 6

| Wt ratio SIBS, SMA/ Kraton | Dry Adhesion (g/in) | Wet adhesion (4 day) (g/in) | Failure Mode |
|---|---|---|---|
| 100/0 | 383 | 300 | Adhesive |
| 90/10 | 629 | 645 | Adhesive |
| 80/20 | 825 | 833 | Adhesive |

Example 9

This example comprises an additional approach in which the adhesion promoting polymer is blended in a single layer with the block copolymer layer. SEBS-g-MA (Kraton® 1901) was hydrolyzed to maleic acid (free acid) via base hydrolysis with KOH followed by acidification of the salt with HCl. The resulting Kraton® free acid polymer (KFA) was evaluated blended with SIBS and SMA (same as described in Example 8) as a single layer. Blends of 70/30 wt/wt SIBS/SMA with 5, 10 and 20 wt % KFA were prepared at 25 wt % solids in toluene and coated to a dry coating thickness of ~60 µm on stainless steel foil. Dry and wet (4 day) adhesion was measured as described above. Adhesion results are shown in the following Table 7. It was found that by converting the maleic anhydride of Kraton® 1901 to the carboxylic acid via base hydrolysis, adhesion could be significantly enhanced relative to anhydride form Kraton® 1901 as purchased.

TABLE 7

| Wt ratio SIBS, SMA/ Kraton free acid | Dry Adhesion (g/in) | Wet adhesion (4 day) (g/in) | Failure Mode |
|---|---|---|---|
| 100/0 | 383 | 300 | Adhesive |
| 95/5 | 1098 | 924 | adhesive |
| 90/10 | 2159 | 1771 | Tensile |
| 80/20 | 2194 | 2011 | tensile |

It is believed that each of the SEBS-g-maleic anhydride and the SEBS-g-maleic acid copolymers enhances adhesion to stainless steel based on the presence of the maleic anhydride and/or maleic acid groups. The SEBS-g-maleic anhydride and the SEBS-g-maleic acid copolymers also share a common monomer with the SIBS (i.e., styrene), which is believed to provide compatibility between the polymers. Also, the maleic anhydride in the SMA of the SIBS/SMA blend is believed to provide compatibility with the maleic anhydride or maleic acid monomers within the adhesion promoting copolymers, whereas the styrene in the SMA of the SIBS/SMA blend is believed to provide improved compatibility with the styrene within the SIBS block copolymer (but not to the point to where it is soluble in SIBS).

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a metallic substrate and a polymeric region disposed over and in contact with the metallic substrate, said polymeric region comprising (a) a block copolymer that comprises (i) a hard polymer block that comprises a high Tg monomer and (ii) a soft polymer block that comprises a low Tg monomer, (b) an adhesion promoting copolymer that comprises (i) a first monomer that covalently or non-covalently bonds with the metallic substrate and (ii) a second monomer that is compatible with the low Tg monomer, the high Tg monomer, or both, and (c) a therapeutic agent.

2. The medical device of claim 1, wherein said polymeric region comprises an adhesion promoting polymeric drug release layer disposed over and in contact with the metallic substrate, said adhesion promoting polymeric drug release layer comprising said block copolymer, said adhesion promoting copolymer and said therapeutic agent.

3. The medical device of claim 1, wherein said polymeric region comprises (a) an adhesion promoting layer comprising said adhesion promoting copolymer disposed over and in contact with the substrate, and (b) a polymeric drug release layer comprising said block copolymer and said therapeutic agent disposed over and in contact with the adhesion promoting layer.

4. The medical device of claim 1, wherein said metallic substrate is selected from a stainless steel substrate, a nitinol substrate, a platinum enriched stainless steel substrate and a substrate formed from an alloy comprising cobalt and chromium.

5. The medical device of claim 1, wherein said low Tg monomer is selected from alkyl acrylate monomers, alkyl methacrylate monomers, alkene monomers, and siloxane monomers.

6. The medical device of claim 5, wherein said low Tg monomer is selected from n-butyl acrylate, n-hexyl acrylate, n-hexyl methacrylate, 2-ethylhexy acrylate, 2-ethylhexyl methacrylate, dodecyl acrylate, dodecyl methacrylate and isobutylene.

7. The medical device of claim 1, wherein said soft polymer block comprises two or more differing low Tg monomers.

8. The medical device of claim 1, wherein said high Tg monomer is selected from alkyl acrylate monomers, alkyl methacrylate monomers, and vinyl aromatic monomers.

9. The medical device of claim 8, wherein said high Tg monomer is selected from methyl methacrylate, ethyl acrylate, ethyl methacrylate and styrene.

10. The medical device of claim 1, wherein said hard polymer block comprises two or more differing high Tg monomers.

11. The medical device of claim 1, wherein said block copolymer comprises a plurality of hard blocks with an intervening soft block.

12. The medical device of claim 11, wherein said block copolymer comprises a soft block main chain and a plurality of hard block side chains spaced along the soft block main chain.

13. The medical device of claim 11, wherein said block copolymer is a linear triblock copolymer comprising a soft block disposed between two hard blocks.

14. The medical device of claim 1, wherein said block copolymer is a star copolymer comprising a soft block disposed between three or more hard blocks.

15. The medical device of claim 1, wherein said block copolymer is a poly(methyl methacrylate-b-n-butyl acrylate-b-methyl methacrylate) triblock copolymer.

16. The medical device of claim 1, wherein said block copolymer is a poly(styrene-b-isobutylene-b-styrene) triblock copolymer.

17. The medical device of claim 16, wherein said poly (styrene-b-isobutylene-b-styrene) triblock copolymer is blended with poly(styrene-co-maleic acid).

18. The medical device of claim 1, wherein said adhesion promoting copolymer is selected from random, periodic, statistical and gradient copolymers.

19. The medical device of claim 1, wherein said adhesion promoting copolymer is a block copolymer.

20. The medical device of claim 1, wherein said second monomer is compatible with said high Tg monomer.

21. The medical device of claim 20, wherein said second monomer is the same as said high Tg monomer.

22. The medical device of claim 1, wherein said second monomer is compatible with said low Tg monomer.

23. The medical device of claim 22, wherein said second monomer is the same as said low Tg monomer.

24. The medical device of claim 22, wherein said adhesion promoting copolymer further comprises a third monomer that is compatible with said high Tg monomer.

25. The medical device of claim 23, wherein said second monomer is the same as said low Tg monomer and wherein said third monomer is the same as said high Tg monomer.

26. The medical device of claim 1, wherein the first monomer covalently bonds with the substrate.

27. The medical device of claim 26, wherein the first monomer comprises a

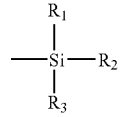

group, where $R_1$, $R_2$ and $R_3$ are independently linear or branched $C_1$-$C_{10}$ alkyl groups, $C_6$-$C_{12}$ aryl groups, or linear or branched $C_1$-$C_{10}$ alkoxy groups, with the proviso that at least one of $R_1$, $R_2$ and $R_3$ is a linear or branched $C_1$-$C_{10}$ alkoxy group.

28. The medical device of claim 27, wherein the first monomer is selected from a vinylalkylalkoxysilane of the formula

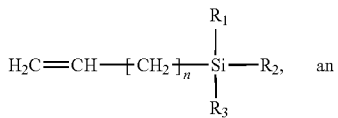 an acryloyloxy(alkylene)alkoxysilane of the formula a

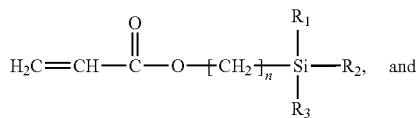 and a methacryloyloxy(alkylene)alkoxysilane of the formula

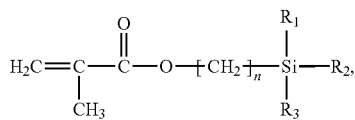

where n is an integer between 0 and 10, and wherein $R_1$, $R_2$ and $R_3$ are defined above.

29. The medical device of claim 1, wherein the first monomer non-covalently bonds with the substrate.

30. The medical device of claim 29, wherein the first monomer is an acidic monomer.

31. The medical device of claim 29, wherein the first monomer comprises a carboxylic acid group, a carboxylic acid anhydride group, a hydroxyl acid group, a sulfonic acid group or a phosphonic acid group.

32. The medical device of claim 31, wherein said first monomer is selected from an acrylic acid monomer, a maleic acid monomer and a maleic anhydride monomer.

33. The medical device of claim 1, wherein said therapeutic agent is selected from antiproliferative agents, antithrombotic agents, endothelial cell growth promoters, antimicrobial agents, analgesic agents, and anti-inflammatory agents.

34. The medical device of claim 1, comprising a plurality of differing therapeutic agents.

35. The medical device of claim 1, wherein said medical device is an implantable or insertable medical device.

36. The medical device of claim 1, wherein said substrate is a metallic stent.

37. The medical device of claim 1, wherein said polymeric region completely covers said substrate.

38. The medical device of claim 1, wherein said polymeric region partially covers said substrate.

39. The medical device of claim 1, wherein said substrate is a metallic stent and wherein the polymeric region covers an outer abluminal surface of the stent, but not an inner luminal surface of the stent.

40. The medical device of claim 1, wherein said polymeric region comprises an additional polymer in admixture with said block copolymer and said therapeutic agent.

41. The medical device of claim 40, wherein said additional polymer is a copolymer comprising (i) a monomer that is compatible with one of said high Tg monomer and said low Tg monomer, and (ii) a monomer that is incompatible with the other of said high Tg monomer and said low Tg monomer.

* * * * *